(12) United States Patent
Markel

(10) Patent No.: US 9,694,046 B2
(45) Date of Patent: Jul. 4, 2017

(54) CEACAM BASED ANTIBACTERIAL AGENTS

(71) Applicant: Gal Markel, Haifa (IL)

(72) Inventor: Gal Markel, Haifa (IL)

(73) Assignee: Gal Markel, Haifa (IL)

( * ) Notice: Subject to any disclaimer, the term of this patent is extended or adjusted under 35 U.S.C. 154(b) by 0 days.

(21) Appl. No.: 13/628,541

(22) Filed: Sep. 27, 2012

(65) Prior Publication Data

US 2013/0123464 A1    May 16, 2013

Related U.S. Application Data

(63) Continuation of application No. 11/679,657, filed on Feb. 27, 2007, now Pat. No. 8,298,544.

(60) Provisional application No. 60/776,970, filed on Feb. 27, 2006.

(51) Int. Cl.
| | | |
|---|---|---|
| A61K 39/00 | (2006.01) | |
| C07K 1/00 | (2006.01) | |
| C07K 2/00 | (2006.01) | |
| A61K 38/08 | (2006.01) | |
| A23L 3/34 | (2006.01) | |
| A23L 3/3526 | (2006.01) | |
| C07K 7/06 | (2006.01) | |
| A23L 33/135 | (2016.01) | |
| A23L 33/195 | (2016.01) | |

(52) U.S. Cl.
CPC .............. *A61K 38/08* (2013.01); *A23L 3/34* (2013.01); *A23L 3/3526* (2013.01); *A23L 33/135* (2016.08); *A23L 33/195* (2016.08); *C07K 7/06* (2013.01)

(58) Field of Classification Search
CPC .................................................. A61K 38/08
See application file for complete search history.

(56) References Cited

U.S. PATENT DOCUMENTS

| | | | |
|---|---|---|---|
| 6,759,045 B2 * | 7/2004 | Goldenberg et al. | 424/153.1 |
| 6,812,339 B1 * | 11/2004 | Venter et al. | 536/24.31 |
| 8,298,544 B2 * | 10/2012 | Markel | 424/185.1 |
| 2008/0242834 A1 * | 10/2008 | Kieliszewski et al. | 530/300 |

OTHER PUBLICATIONS

Muchova et al (Biomedical Chromatography vol. 15, pp. 418-422, 2001).*

* cited by examiner

*Primary Examiner* — Albert Navarro
(74) *Attorney, Agent, or Firm* — McAndrews, Held & Malloy

(57) ABSTRACT

Prophylactic and/or therapeutic antipathogen agents are provided that disrupt or prevent the formation of at least one homotypic and/or heterotypic protein-protein interaction that has at least one CEA-family protein and that is involved in the establishment and colonization of a pathogen in a suitable host.

2 Claims, No Drawings

CEACAM BASED ANTIBACTERIAL AGENTS

RELATED APPLICATIONS

The present application is a continuation of U.S. patent application Ser. No. 11/679,657 filed Feb. 27, 2007, which is related to and claims priority from U.S. Provisional Patent Application Ser. No. 60/776,970, filed Feb. 27, 2006, and titled "CEACAM1 BASED ANTIMICROBIAL AGENT," the contents of which are expressly incorporated herein by reference in their entirety. Additionally, all cited references in the present application are hereby incorporated by reference in their entirety.

BACKGROUND OF THE INVENTION

The technology of the present invention relates to the treatment, prevention, and/or decrease in the incidence of infection by a pathogenic agent. In particular, certain aspects of the present technology relate to the prevention of the colonization by a pathogen.

Examples of pathogens include microorganisms such as bacteria, viruses, protozoa, or fungi that can cause disease. Pathogens may be endogenous or exogenous. The clinical presentation of an infectious disease state reflects the interaction between the host and the microorganism. This interaction is affected by several factors including for example the host immune status and microbial virulence factors. Signs and symptoms can vary according to the site and severity of infection. The responsibility of the medical microbiology laboratory includes not only microbial detection, isolation, and identification, but also the determination of microbial susceptibility to select antimicrobial agents.

Antimicrobial agents, or antipathogen agents, generally kill, slow the growth, and/or inhibit the pathogenic action of microbes or pathogens. Included among the antimicrobial agents are antibacterial agents, antiviral agents, antifungal agents, and antiparisitic agents. In spite of the availability of effective antimicrobial drugs and vaccines, the battle against infectious diseases is far from being over. Particularly in developing countries, the emergence and spread of antimicrobial resistance is threatening to undermine the ability to treat infections and save lives. The development of new families of antimicrobials throughout the 1950s and 1960s and of modifications of these molecules through the 1970s and 1980s allowed the medical community to believe that it could always remain ahead of the pathogens. However, the pipeline of new drugs is running short and there is an impetus to develop new antimicrobials to address the global problems of drug resistance.

In addition to establishing effective public health policies regarding the proper use of antimicrobial agents, there is a general consensus that continued research and development of new antimicrobial agents is vital to keeping pace with the evolution of resistant pathogenic microbes. Over and above research regarding pharmacokinetics, pharmacodynamics, and dosage regimens, research into the identification and function of novel genes to provide the industry with new and defined targets for therapeutic intervention is paramount.

Pathogens constitute a diverse set of agents. There are correspondingly diverse ranges of mechanisms by which pathogens cause disease. The survival of most pathogens require that they colonize the host, reach an appropriate niche, avoid host defenses, replicate, and exit the infected host to spread to an uninfected one. In particular, many bacteria have unpredictable susceptibilities to antibacterial agents, and antibacterial resistance continues to cause a large number of sustained infections and deaths. Evolution of bacteria towards resistance to antimicrobial drugs, including multidrug resistance, is unavoidable because it represents a particular aspect of the general evolution of bacteria that is unstoppable. Resistance to antimicrobial drugs in bacteria can result from mutations in housekeeping structural or regulatory genes. Alternatively, resistance can result from the horizontal acquisition of foreign genetic information. The two phenomena are not mutually exclusive and can be associated in the emergence and more efficient spread of resistance.

The progression of a pathogenic bacterial infection to a disease state generally includes entry, colonization, and growth. Most infections begin with the adherence of bacteria to specific cells on the mucous membranes of the respiratory, alimentary, or genitourinary tract. Many bacteria possess surface macromolecules that bind to complementary acceptor molecules on the surfaces of certain animal cells, thus promoting specific and firm adherence. Certain of these macromolecules are polysaccharides and form a meshwork of fibers called the glycocalyx. Other proteins are specific, (e.g., M-proteins on the surface of *Streptococcus pyogenes*) which facilitate binding to the respiratory mucosal receptor. Also structures known as fimbrae may be important in the attachment process. For example, the fimbrae of *Neiseria gonorrhoeae* play a key role in the attachment of this organism to the urogenital epithelium where it causes a sexually transmitted disease. Also, it has been shown that fimbriated strains of *Escherichia coli* are much more frequent causes of urinary tract infections than strains lacking fimbrae, showing that these structures can indeed promote the capacity of bacteria to cause infection.

If a pathogen gains access to tissues by adhesion and invasion it typically multiplies by a process called colonization. Colonization typically requires that the pathogen first bind to specific tissue surface receptors and overcome any host defenses. The initial inoculum may or may not be sufficient to cause damage. A pathogen generally must grow within host tissues in order to produce disease.

The human CEA-protein family of proteins (Carcinoembryonic antigen-related) is expressed on the internal cellular lining of the gastrointestinal tract and is most likely exploited by some bacterial pathogens for colonization. The human CEA-protein family includes several distinct proteins, such as the CEACAM1 (Carcinoembryonic antigen-related cell adhesion molecule 1), CEACAM3, CEACAM5, CEACAM6 and CEACAM8. Each of these proteins has a unique expression distribution among different cells and tissues, and can interact with various target molecules, including some of the CEA protein themselves. These interactions generate a broad variety of biological functions. So far, several functions have been attributed to CEA proteins, including without limitation, the regulation of endocrine, immunologic, and cancerous processes, as well as tissue structure organization.

Various CEA proteins interact with different bacterial strains, including without limitation, some *E. coli* (an entire group of enteric bacteria), *N. gonorrhea* (causes gonorrhea), *N. meningitides* (causes severe meningitis), *M. catarrhalis* (causes upper respiratory infections, pneumonia and otitis media). These pathogens generally must first adhere to the appropriate internal cellular lining before causing the actual disease, in a process generally known as colonization Adding to the medical community's repertoire of available antipathogen agents, and that community's ability to fight the problem of antibacterial resistance, the present technology is directed in part to the development of new antipathogen agents derived from the human CEA-protein family of proteins or derivatives thereof. In particular, the present technology is directed to the use of human CEA-proteins, or derivatives thereof, for the prevention or retardation of a pathogenic infection, including bacterial and viral infection, and the subsequent progression to a virulent disease state.

BRIEF SUMMARY OF THE INVENTION

One object of the present invention is to provide methods, agents, and compositions for preventing and/or treating infection by a pathogen. Another object of the present invention is to provide methods, agents, and compositions for preventing colonization by a pathogen.

One or more of the preceding objects, or one or more other objects which will become plain upon consideration of the present specification, are satisfied by the invention described herein.

One aspect of the invention is a prophylactic and/or therapeutic antipathogen agent that disrupts the formation of at least one homotypic and/or heterotypic protein-protein interaction involved in the progression and/or colonization of a pathogen during infection. Another aspect of the invention, is a prophylactic and/or therapeutic agent that disrupts the formation of at least one homotypic and/or heterotypic protein-protein interaction involving at least one CEA-family protein. An agent can disrupt the formation of a protein-protein complex by preventing, interfering, slowing, reducing, or altering the equilibrium of the formation, including combinations of the forgoing.

Another aspect of the invention is a method for treating or preventing infection by a pathogen. A still further aspect of the invention is the use of an antipathogen agent for the manufacture of a medicament to treat or prevent infection by a pathogen.

In some embodiments, the antipathogen agent comprises an amino acid sequence, such as a sequence derived from a CEA-family protein sequence. A sequence is derived from another sequence when it includes some or all of the amino acids in the same order. An amino acid sequence may be a protein, peptide, polypeptide, or peptidomimetic.

DETAILED DESCRIPTION OF THE INVENTION

The present invention provides for the prevention or treatment of infection by a pathogen or combination of pathogens. As used herein a pathogen includes any endogenous or exogenous causative agent of disease. Pathogens include but are not limited to bacteria, viruses, yeast, protozoa, fungi, or any combination or derivative thereof. For example, bacterial pathogens include without limitation any *E. coli* species, *Niesseria* species, *Moraxella* species, *Salmonella* species, or any combination or derivative thereof. Exemplar viral pathogens include but are not limited to Cytomegalovirus (CMV).

The process of infection by a pathogen generally includes but is not limited to the establishment of a pathogen in or on a suitable host. The process by which a pathogen is established in or on a suitable host generally includes without limitation the association or attachment of the pathogen to a suitable host surface followed by colonization. An infection by a pathogen can occur in or on any region of the host. Infection by a pathogen can occur in or on any region of the host, including for example the skin, respiratory tract, gastrointestinal track, or any combination thereof. Infection by a pathogen can occur in or on any region of the host, including without limitation any system of the body, such as for example the skeletal, muscular, nervous, endocrine, cardiovascular, lymphatic, respiratory, digestive, urinary, reproductive, or any combination thereof. The host can be human or any lower animal, including both domestic and non-domestic animals.

One aspect of the invention is a prophylactic and/or therapeutic antipathogen agent that disrupts the formation of at least one CEA-family protein homotypic and/or heterotypic protein-protein interaction that is involved in the establishment of a pathogen in or on a suitable host and/or the progression to a disease state. As used herein a CEA-family protein includes but is not limited to CEACAM1, CEACAM3, CEACAM5, CEACAM6 and CEACAM8. An agent can disrupt the formation of a protein-protein complex by preventing, interfering, slowing, reducing, or altering the equilibrium of the formation, including combinations of the forgoing.

One aspect of the invention is a prophylactic and/or therapeutic antipathogen composition having at least one antipathogen agent that disrupts the formation of at least one homotypic and/or heterotypic protein-protein interaction that includes at least one CEA-family protein and that is involved in the establishment of a pathogen in or on a suitable host and/or the progression to a disease state. As used herein a CEA-family protein includes but is not limited to CEACAM1, CEACAM3, CEACAM5, CEACAM6 and CEACAM8.

The antipathogen agents of the present invention include but are not limited to protein, polypeptide, peptide, nucleic acid, large molecule, small molecule, derivatives and/or fragments thereof, and combinations thereof. The term "large molecule", as used herein, refers to organic or inorganic molecules either synthesized or found in nature, generally having a molecular weight greater than 1000, however the definition of large molecule is not limited by this number. The term "small molecule", as used herein, refers to organic or inorganic molecules either synthesized or found in nature, generally having a molecular weight equal to or less than 1000, however the definition of small molecule is not limited by this number.

The antipathogen agents of the present invention generally comprise at least one structural motif that prevents the formation of a protein-protein complex, or disrupts an already formed protein-protein complex, that is directly or indirectly associated with the establishment of a pathogen in or on a suitable host. As used herein, the term structural motif generally refers to any distinct grouping of chemical elements having a structure chosen based on a specified function.

The term protein includes any of various substances that comprise amino-acid residues joined by peptide bonds. The term protein includes polypeptides and peptides. The terms protein, polypeptide, peptide and "nucleic acid" include compositions of the invention that also include "analogs," or "conservative variants" and "mimetics" such as "peptidomimetics" with structures and activity that substantially correspond to the compound from which the variant was derived. For example, in some aspects of the present invention, the use of peptoids derived from one or more CEACAM protein sequences is contemplated. The synthesis and use of peptoids have previously been described in U.S. Pat. No. 5,811,387 "Peptoid mixtures" and U.S. Pat. No. 5,831,005 "Synthesis of N-substituted oligomers." These references are herein incorporated by reference.

The antipathogen agents of the present invention can be without limitation any reversible or non-reversible, competitive or non-competitive, inhibitor of the formation and/or maintenance (stability) of any homotypic and/or heterotypic protein-protein interaction that includes at least one CEA-family protein and that is involved in the establishment of a pathogen in or on a suitable host and/or the progression to a disease state.

In one embodiment of the present invention, the antipathogen agent has at least one peptide bond. These antipathogen agents include but are not limited to full-length proteins, protein structural or functional domains, smaller peptides, and peptidomimetic derivatives. For Example, these antipathogen agents can be derived from any host or pathogen protein that participates in any homotypic and/or heterotypic protein-protein interaction that is involved in the progression of a pathogen infection, including for example the adhesion, invasion, and/or establishment of a pathogen in or on a suitable host.

In one embodiment of the present invention, the antipathogen agent is a full length CEA-family protein, or a fragment derived therefrom. CEA-family proteins that can be used as antipathogen agents include but are not limited to the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein represented by SEQ ID No. 5.

In another embodiment of the present invention, the antipathogen agent comprises a fragment of a CEA-family protein. CEA-family protein fragments that can be used as antipathogen agents include but are not limited to the CEACAM1 domain 1 (Ig-like V-type N-domain) represented by SEQ ID No. 6; the CEACAM1 domain 2 (Ig-like C2-type 1) represented by SEQ ID No. 7; the CEACAM1 domain 3 (Ig-like C2-type 2) represented by SEQ ID No. 8; the CEACAM1 domain 4 (Ig-like C2-type 3) represented by SEQ ID No. 9; the CEACAM6 domain 1 (Ig-like V-type N-domain) represented by SEQ ID No. 10; the CEACAM6 domain 2 (Ig-like C2-type 1) represented by SEQ ID No. 11; the CEACAM6 domain 3 (Ig-like C2-type 2) represented by SEQ ID No. 12; CEACAM5 domain 1 (Ig-like V-type N-domain) represented by SEQ ID No. 13; the CEACAM5 domain 2 (Ig-like C2-type 1) represented by SEQ ID No. 14; the CEACAM5 domain 3 (Ig-like C2-type 2) represented by SEQ ID No. 15; the CEACAM5 domain 4 (Ig-like C2-type 3) represented by SEQ ID No. 16; the CEACAM5 domain 5 (Ig-like C2-type 4) represented by SEQ ID No. 17; the CEACAM5 domain 6 (Ig-like C2-type 5) represented by SEQ ID No. 18; and the CEACAM5 domain 7 (Ig-like C2-type 6) represented by SEQ ID No. 19.

In another embodiment of the present invention, the antipathogen agent is a full-length pathogen protein, or a fragment or domain derived therefrom. Pathogen proteins, protein domains, or protein fragments that can be used as antipathogen agents include but are not limited to those that are exposed on the bacterial cell surface and that participate in the adhesion, invasion, and/or establishment of a pathogen in or on a suitable host. For example, the *Moraxella catarrhalis* surface protein UspA1 represented by SEQ ID No. 20, or any domain, fragment or derivative thereof that binds to *Moraxella catarrhalis*, can be used as a *Moraxella catarrhalis* specific antipathogen agent. The *Neisseria meningitidis* opacity (Opa) proteins, including any domains, fragments or derivatives thereof, can also be used as *Neisseria meningitidis* specific antipathogen agents.

In another embodiment of the present invention, the antipathogen agent comprises a short linear or cyclic peptide. The peptide can be derived from any host or pathogen protein that participates in any homotypic and/or heterotypic protein-protein interaction that is involved in the progression of a pathogen infection, including for example the adhesion, invasion, and/or establishment of a pathogen in or on a suitable host. Exemplar peptides that can be used as antipathogen agents include but are not limited to the peptide NRQIV (SEQ ID No. 21) found in the CEACAM1 protein represented by SEQ ID No. 1; the peptide NRQII (SEQ ID No. 22) found in the CEACAM5 protein represented by SEQ ID No. 3; and the QNDTG peptide (SEQ ID No. 23) and the GYSWYK peptide (SEQ ID No. 24) both found in the CEACAM1 protein represented by SEQ ID No. 1, the CEACAM5 protein represented by SEQ ID No. 3, and the CEACAM6 protein represented by SEQ ID No. 4.

In another embodiment of the present invention, the antipathogen agent comprises a derivative of a peptide sequence found in the sequence of a CEACAM family protein, such as for example the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein represented by SEQ ID No. 5. In a further embodiment of the present invention, the antipathogen agent is a derivative of a peptide sequence found in the sequence of a protein expressed by a pathogen of interest and involved in the colonization of that pathogen in a host. Derivatives of any of the sequences disclosed herein can be identified, which display different binding kinetics and specificities, using standard directed evolution methods that are well known in the art. For example directed evolution methods including an iterative process of mutagenesis, expression, chromatographic selection, and amplification for the identification of new peptides having selective binding activities can be employed (Kay, B. K. et al. (2001) "Screening phage-displayed combinatorial peptide libraries." *Methods* 24, 240-246.) In certain embodiments of the present invention, the peptide NRQIV found in the CEACAM1 protein represented by SEQ ID No. 1; the peptide NRQII found in the CEACAM5 protein represented by SEQ ID No. 3; and the QNDTG peptide and the GYSWYK peptide both found in the CEACAM1 protein represented by SEQ ID No. 1, the CEACAM5 protein represented by SEQ ID No. 3, and the CEACAM6 protein represented by SEQ ID No. 4 can be used as the basic scaffold in a directed evolution experiment designed to identify different peptides having a different binding specificities and/or kinetics. For example, the Ph.D™ Phage Display Cloning System from New England Biolabs can be used to create CEACAM derived peptide libraries on the surface of bacteriophage M13 as coat protein fusions, creating a physical linkage between each displayed peptide and its encoding DNA sequence, and which allows rapid partitioning based on binding affinity to a given target molecule (such as a pathogen protein) by an in vitro selection process called panning (Whaley, S. R. et al. (2000) *Nature*, 405, 665-668.)

In another embodiment of the present invention, the antipathogen agent comprises a small molecule compound. The term "small molecule" includes any small molecule, either synthesized or found in nature, such as an organic molecule, inorganic molecule, or a synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867-873. This reference is herein incorporated by reference. Synthesis of small molecules, as with all other procedures associated with this invention, can be practiced in conjunction with any method or protocol known in the art. For example, preparation and screening of combinatorial chemical libraries are well known, see, e.g., U.S. Pat. Nos. 6,096,496; 6,075,166; 6,054,047; 6,004,617; 5,985,356; 5,980,839; 5,917,185; 5,767,238. These references are herein incorporated by reference.

In a further embodiment of the present invention, the antipathogen agent comprises derived from a random library of compounds by selection or screening. The compounds include but are not limited to compounds having at least one peptide bond, nucleic acids, large molecules, small molecules, or any combinations or derivatives thereof.

In another embodiment of the present invention, the antipathogen agent comprises a multimer antipathogen agent comprising at least two or more antipathogen agents, according to the present invention, linked together. The antipathogen agents, linked together to form the multimer antipathogen agent, can be identical or different, and can include but are not limited to any combination of protein, nucleic acid, large molecule, small molecule, or derivatives thereof.

In certain embodiments of the present invention, the antipathogen is formulated in a suitable dosage form. Dosage forms include but are not limited to pills, dragees, tablets, capsules, solutions, liquids, slurries, suspensions, suppositories, emulsions, troches, transdermal patches, oral powders, oral mists, and oral strips. Any suitable material can be used to make the dosage form, including for example starch, sucrose, maltose, maltodextrin, and saccharin. Any suitable route of administration can be employed including for example oral, inhaled, intravenous, intramuscular, intra-arterial, intramedullary, intrathecal, intraventricular, subcutaneous, intraperitoneal, transdermal, intradermal, intranasal, jejunal, topical, sublingual, and/or rectal.

In still other embodiments, antipathogen agents according to the present invention can be added to solid foodstuffs, liquid foodstuffs, powdered foodstuffs, medicinal solutions, non-medicinal solutions, medicinal aerosols, non-medicinal aerosols, non-animate solid surfaces, or any combination or derivative thereof.

In other embodiments, antipathogen agents according to the present invention can be added to a nutraceutical composition. As used herein, a nutraceutical is any foodstuff that provides health benefits, including without limitation a fortified food or dietary supplement. A nutraceutical includes but is not limited to any substance that can be considered a food or part of a food and provides medical or health benefits, including the prevention and treatment of disease.

In one particular embodiment of the present invention, commercial milk remedies for children are supplemented with the antipathogen agents of the present invention, including for example those that are specific for those pathogens causing childhood diseases such as diarrhea, bacterial meningitis and bacterial upper respiratory infections. Examples of pathogens include without limitation pathogenic *E. coli* that cause, for example, diarrhea. Pathogens also include but are not limited to *Neisseria* species, including for example *N. gonorrhoeae* and *N. meningitidis*, *Moraxella Catarrhalis* and *Haemophilus* species, including for example, *H. influenza*.

In yet another embodiment, probiotics can be genetically engineered to produce one or more of the antipathogen agents of the present invention. Probiotics include without limitation live bacterial preparations having clinical health effects when presented to a host. Probiotics can be derived or engineered from bacteria that normally inhabit the gastrointestinal system of the host, or bacteria typically associated with dairy fermentation and fermented dairy products. For example, the probiotic can be derived from, or engineered from bacteria of the genera *Lactobacillus, Bifidobacterium, Escherichia, Enterococcus,* or *Bacillus*. The probiotic can be presented for example as a culture concentrate, or inoculated into a milk-based food. The probiotic can also be formulated as concentrated and dried cells packaged as dietary additives.

A still further aspect of the present invention regards increasing the uptake of lipids in the human gastrointestinal (GI) tract. This aspect of the invention can be achieved by contacting the GI track with the CEACAM1 protein and/or derivatives of the CEACAM1 protein. For example, the CEACAM1 protein and/or derivatives of the CEACAM1 protein can be added in soluble or non-soluble form to any dietary source of lipids. As used herein, in connection with this aspect of the present invention, a lipid includes without limitation a relatively water-insoluble or nonpolar compound such as micelles, fatty acids, fatty-acid derived phospholipids, sphingolipids, glycolipids and terpenoids, such as retinoids and steroids.

What is claimed is:

1. A multimer therapeutic agent consisting of the isolated peptide SEQ ID No. 24 and at least two additional isolated peptides selected from the group consisting of SEQ ID No. 21-SEQ ID No. 23.

2. A multimer therapeutic agent consisting of the isolated peptide SEQ ID No. 24 and at least two additional isolated peptides selected from sequence NRQIV (SEQ ID No. 21) and QNDTG (SEQ ID No. 23).

* * * * *

SEQUENCE LISTING

```
<160> NUMBER OF SEQ ID NOS: 24

<210> SEQ ID NO 1
<211> LENGTH: 526
<212> TYPE: PRT
<213> ORGANISM: Homo Sapiens
<220> FEATURE:
<221> NAME/KEY: MISC_FEATURE
<223> OTHER INFORMATION: NCBI accession number P13688

<400> SEQUENCE: 1

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30
```

-continued

Thr Ala Gln Leu Thr Thr Glu Ser Met Pro Phe Asn Val Ala Glu Gly
         35                  40                  45

Lys Glu Val Leu Leu Val His Asn Leu Pro Gln Gln Leu Phe Gly
 50                  55                  60

Tyr Ser Trp Tyr Lys Gly Glu Arg Val Asp Gly Asn Arg Gln Ile Val
 65                  70                  75                  80

Gly Tyr Ala Ile Gly Thr Gln Gln Ala Thr Pro Gly Pro Ala Asn Ser
                 85                  90                  95

Gly Arg Glu Thr Ile Tyr Pro Asn Ala Ser Leu Leu Ile Gln Asn Val
                100                 105                 110

Thr Gln Asn Asp Thr Gly Phe Tyr Thr Leu Gln Val Ile Lys Ser Asp
             115                 120                 125

Leu Val Asn Glu Glu Ala Thr Gly Gln Phe His Val Tyr Pro Glu Leu
         130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                 165                 170                 175

Leu Trp Trp Ile Asn Asn Gln Ser Leu Pro Val Ser Pro Arg Leu Gln
             180                 185                 190

Leu Ser Asn Gly Asn Arg Thr Leu Thr Leu Leu Ser Val Thr Arg Asn
         195                 200                 205

Asp Thr Gly Pro Tyr Glu Cys Glu Ile Gln Asn Pro Val Ser Ala Asn
     210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                 245                 250                 255

Leu Ser Cys Tyr Ala Ala Ser Asn Pro Pro Ala Gln Tyr Ser Trp Leu
             260                 265                 270

Ile Asn Gly Thr Phe Gln Gln Ser Thr Gln Glu Leu Phe Ile Pro Asn
         275                 280                 285

Ile Thr Val Asn Asn Ser Gly Ser Tyr Thr Cys His Ala Asn Asn Ser
     290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                 325                 330                 335

Val Thr Gly Asp Lys Asp Ser Val Asn Leu Thr Cys Ser Thr Asn Asp
             340                 345                 350

Thr Gly Ile Ser Ile Arg Trp Phe Phe Lys Asn Gln Ser Leu Pro Ser
         355                 360                 365

Ser Glu Arg Met Lys Leu Ser Gln Gly Asn Thr Thr Leu Ser Ile Asn
     370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                 405                 410                 415

Asn Ala Leu Pro Gln Glu Asn Gly Leu Ser Pro Gly Ala Ile Ala Gly
             420                 425                 430

Ile Val Ile Gly Val Val Ala Leu Val Ala Leu Ile Ala Val Ala Leu
         435                 440                 445

```
Ala Cys Phe Leu His Phe Gly Lys Thr Gly Arg Ala Ser Asp Gln Arg
            450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
                500                 505                 510

Leu Thr Ala Thr Glu Ile Ile Tyr Ser Glu Val Lys Lys Gln
            515                 520                 525

<210> SEQ ID NO 2
<211> LENGTH: 292
<212> TYPE: PRT
<213> ORGANISM: Homo Sapiens
<220> FEATURE:
<221> NAME/KEY: MISC_FEATURE
<223> OTHER INFORMATION: NCBI accession number AAQ88451

<400> SEQUENCE: 2

Met Gly Pro Pro Ser Ala Cys Pro His Arg Glu Cys Ile Pro Trp Gln
1               5                   10                  15

Gly Leu Leu Leu Thr Ala Ser Leu Leu Thr Phe Trp Asn Ala Pro Thr
            20                  25                  30

Thr Ala Trp Leu Phe Ile Ala Ser Ala Pro Phe Glu Val Ala Glu Gly
        35                  40                  45

Glu Asn Val His Leu Ser Val Val Tyr Leu Pro Glu Asn Leu Tyr Ser
50                  55                  60

Tyr Gly Trp Tyr Lys Gly Lys Thr Val Glu Pro Asn Gln Leu Ile Ala
65                  70                  75                  80

Ala Tyr Val Ile Asp Thr His Val Arg Thr Pro Gly Pro Ala Tyr Ser
                85                  90                  95

Gly Arg Glu Thr Ile Ser Pro Ser Gly Asp Leu His Phe Gln Asn Val
            100                 105                 110

Thr Leu Glu Asp Thr Gly Tyr Tyr Asn Leu Gln Val Thr Tyr Arg Asn
        115                 120                 125

Ser Gln Ile Glu Gln Ala Ser His His Leu Arg Val Tyr Glu Ser Val
130                 135                 140

Ala Gln Pro Ser Ile Gln Ala Ser Ser Thr Thr Val Thr Glu Lys Gly
145                 150                 155                 160

Ser Val Val Leu Thr Cys His Thr Asn Asn Thr Gly Thr Ser Phe Gln
                165                 170                 175

Trp Ile Phe Asn Asn Gln Arg Leu Gln Val Thr Lys Arg Met Lys Leu
            180                 185                 190

Ser Trp Phe Asn His Val Leu Thr Ile Asp Pro Ile Arg Gln Glu Asp
        195                 200                 205

Ala Gly Glu Tyr Gln Cys Glu Val Ser Asn Pro Val Ser Ser Asn Arg
210                 215                 220

Ser Asp Pro Leu Lys Leu Thr Val Lys Tyr Asp Asn Thr Leu Gly Ile
225                 230                 235                 240

Leu Ile Gly Val Leu Val Gly Ser Leu Leu Val Ala Ala Leu Val Cys
                245                 250                 255

Phe Leu Leu Leu Arg Lys Thr Gly Arg Ala Ser Asp Gln Ser Asp Phe
            260                 265                 270
```

Arg Glu Gln Gln Pro Pro Ala Ser Thr Pro Gly His Gly Pro Ser Asp
        275                 280                 285

Ser Ser Ile Ser
        290

<210> SEQ ID NO 3
<211> LENGTH: 702
<212> TYPE: PRT
<213> ORGANISM: Homo Sapiens
<220> FEATURE:
<221> NAME/KEY: MISC_FEATURE
<223> OTHER INFORMATION: NCBI accession number P06731

<400> SEQUENCE: 3

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

```
Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
    355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
            450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
                500                 505                 510

Val Glu Asp Lys Asp Ala Val Ala Phe Thr Cys Glu Pro Glu Ala Gln
            515                 520                 525

Asn Thr Thr Tyr Leu Trp Trp Val Asn Gly Gln Ser Leu Pro Val Ser
            530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
                580                 585                 590

Pro Asp Thr Pro Ile Ile Ser Pro Pro Asp Ser Ser Tyr Leu Ser Gly
            595                 600                 605

Ala Asn Leu Asn Leu Ser Cys His Ser Ala Ser Asn Pro Ser Pro Gln
            610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
            675                 680                 685

Val Gly Ile Met Ile Gly Val Leu Val Gly Val Ala Leu Ile
            690                 695                 700

<210> SEQ ID NO 4
<211> LENGTH: 344
<212> TYPE: PRT
<213> ORGANISM: Homo Sapiens
<220> FEATURE:
<221> NAME/KEY: MISC_FEATURE
<223> OTHER INFORMATION: NCBI accession number P40199
```

<400> SEQUENCE: 4

```
Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
            35                  40                  45

Lys Glu Val Leu Leu Ala His Asn Leu Pro Gln Asn Arg Ile Gly
50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
                100                 105                 110

Thr Gln Asn Asp Thr Gly Phe Tyr Thr Leu Gln Val Ile Lys Ser Asp
                115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
                180                 185                 190

Leu Ser Asn Gly Asn Met Thr Leu Thr Leu Leu Ser Val Lys Arg Asn
                195                 200                 205

Asp Ala Gly Ser Tyr Glu Cys Glu Ile Gln Asn Pro Ala Ser Ala Asn
            210                 215                 220

Arg Ser Asp Pro Val Thr Leu Asn Val Leu Tyr Gly Pro Asp Val Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
                260                 265                 270

Ile Asn Gly Thr Phe Gln Gln Ser Thr Gln Glu Leu Phe Ile Pro Asn
                275                 280                 285

Ile Thr Val Asn Asn Ser Gly Ser Tyr Met Cys Gln Ala His Asn Ser
                290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
                340
```

<210> SEQ ID NO 5
<211> LENGTH: 349
<212> TYPE: PRT
<213> ORGANISM: Homo Sapiens
<220> FEATURE:
<221> NAME/KEY: MISC_FEATURE
<223> OTHER INFORMATION: NCBI accession number P31997

```
<400> SEQUENCE: 5

Met Gly Pro Ile Ser Ala Pro Ser Cys Arg Trp Arg Ile Pro Trp Gln
1               5                   10                  15

Gly Leu Leu Leu Thr Ala Ser Leu Phe Thr Phe Trp Asn Pro Pro Thr
            20                  25                  30

Thr Ala Gln Leu Thr Ile Glu Ala Val Pro Ser Asn Ala Ala Glu Gly
        35                  40                  45

Lys Glu Val Leu Leu Val His Asn Leu Pro Gln Asp Pro Arg Gly
    50                  55                  60

Tyr Asn Trp Tyr Lys Gly Glu Thr Val Asp Ala Asn Arg Arg Ile Ile
65                  70                  75                  80

Gly Tyr Val Ile Ser Asn Gln Gln Ile Thr Pro Gly Pro Ala Tyr Ser
                85                  90                  95

Asn Arg Glu Thr Ile Tyr Pro Asn Ala Ser Leu Leu Met Arg Asn Val
            100                 105                 110

Thr Arg Asn Asp Thr Gly Ser Tyr Thr Leu Gln Val Ile Lys Leu Asn
        115                 120                 125

Leu Met Ser Glu Glu Val Thr Gly Gln Phe Ser Val His Pro Glu Thr
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Arg Thr Leu Thr Leu Ser Val Thr Arg Asn
        195                 200                 205

Asp Val Gly Pro Tyr Glu Cys Glu Ile Gln Asn Pro Ala Ser Ala Asn
210                 215                 220

Phe Ser Asp Pro Val Thr Leu Asn Val Leu Tyr Gly Pro Asp Ala Pro
225                 230                 235                 240

Thr Ile Ser Pro Ser Asp Thr Tyr Tyr His Ala Gly Val Asn Leu Asn
                245                 250                 255

Leu Ser Cys His Ala Ala Ser Asn Pro Pro Ser Gln Tyr Ser Trp Ser
            260                 265                 270

Val Asn Gly Thr Phe Gln Gln Tyr Thr Gln Lys Leu Phe Ile Pro Asn
        275                 280                 285

Ile Thr Thr Lys Asn Ser Gly Ser Tyr Ala Cys His Thr Thr Asn Ser
290                 295                 300

Ala Thr Gly Arg Asn Arg Thr Thr Val Arg Met Ile Thr Val Ser Asp
305                 310                 315                 320

Ala Leu Val Gln Gly Ser Ser Pro Gly Leu Ser Ala Arg Ala Thr Val
                325                 330                 335

Ser Ile Met Ile Gly Val Leu Ala Arg Val Ala Leu Ile
            340                 345

<210> SEQ ID NO 6
<211> LENGTH: 98
<212> TYPE: PRT
<213> ORGANISM: Homo Sapiens
<220> FEATURE:
<221> NAME/KEY: MISC_FEATURE
<223> OTHER INFORMATION: CEACAM1 domain #1 (Ig-like V-type N-domain)
```

<400> SEQUENCE: 6

Gln Leu Thr Thr Glu Ser Met Pro Phe Asn Val Ala Glu Gly Lys Glu
1               5                   10                  15

Val Leu Leu Leu Val His Asn Leu Pro Gln Glu Arg Val Asp Gly Asn
            20                  25                  30

Arg Gln Ile Val Gly Tyr Ala Ile Gly Thr Gln Gln Ala Thr Pro Gly
        35                  40                  45

Pro Ala Asn Ser Gly Arg Glu Thr Ile Tyr Pro Asn Ala Ser Leu Leu
    50                  55                  60

Ile Gln Asn Val Thr Gln Asn Asp Thr Gly Phe Tyr Thr Leu Gln Val
65                  70                  75                  80

Ile Lys Ser Asp Leu Val Asn Glu Glu Ala Thr Gly Gln Phe His Val
                85                  90                  95

Tyr Pro

<210> SEQ ID NO 7
<211> LENGTH: 91
<212> TYPE: PRT
<213> ORGANISM: Homo Sapiens
<220> FEATURE:
<221> NAME/KEY: MISC_FEATURE
<223> OTHER INFORMATION: CEACAM1 domain #2 (Ig-like C2-type 1)

<400> SEQUENCE: 7

Pro Lys Pro Ser Ile Ser Ser Asn Asn Ser Asn Pro Val Glu Asp Lys
1               5                   10                  15

Asp Ala Val Ala Phe Thr Cys Glu Pro Glu Thr Gln Asp Thr Thr Tyr
            20                  25                  30

Leu Trp Trp Ile Asn Asn Gln Ser Leu Pro Val Ser Pro Arg Leu Gln
        35                  40                  45

Leu Ser Asn Gly Asn Arg Thr Leu Thr Leu Leu Ser Val Thr Arg Asn
    50                  55                  60

Asp Thr Gly Pro Tyr Glu Cys Glu Ile Gln Asn Pro Val Ser Ala Asn
65                  70                  75                  80

Arg Ser Asp Pro Val Thr Leu Asn Val Thr Tyr
                85                  90

<210> SEQ ID NO 8
<211> LENGTH: 81
<212> TYPE: PRT
<213> ORGANISM: Homo Sapiens
<220> FEATURE:
<221> NAME/KEY: MISC_FEATURE
<223> OTHER INFORMATION: CEACAM1 domain #3 (Ig-like C2-type 2)

<400> SEQUENCE: 8

Pro Asp Thr Pro Thr Ile Ser Pro Ser Asp Thr Tyr Tyr Arg Pro Gly
1               5                   10                  15

Ala Asn Leu Ser Leu Ser Cys Tyr Ala Ala Ser Asn Pro Pro Ala Gln
            20                  25                  30

Tyr Ser Trp Leu Ile Asn Gly Thr Phe Gln Gln Ser Thr Gln Glu Leu
        35                  40                  45

Phe Ile Pro Asn Ile Thr Val Asn Asn Ser Gly Ser Tyr Thr Cys His
    50                  55                  60

Ala Asn Asn Ser Val Thr Gly Cys Asn Arg Thr Thr Val Lys Thr Ile
65                  70                  75                  80

Ile

<210> SEQ ID NO 9
<211> LENGTH: 91
<212> TYPE: PRT
<213> ORGANISM: Homo Sapiens
<220> FEATURE:
<221> NAME/KEY: MISC_FEATURE
<223> OTHER INFORMATION: CEACAM1 domain #4 (Ig-like C2-type 3)

<400> SEQUENCE: 9

Pro Val Val Ala Lys Pro Gln Ile Lys Ala Ser Lys Thr Thr Val Thr
1               5                   10                  15

Gly Asp Lys Asp Ser Val Asn Leu Thr Cys Ser Thr Asn Asp Thr Gly
            20                  25                  30

Ile Ser Ile Arg Trp Phe Phe Lys Asn Gln Ser Leu Pro Ser Ser Glu
        35                  40                  45

Arg Met Lys Leu Ser Gln Gly Asn Thr Thr Leu Ser Ile Asn Pro Val
50                  55                  60

Lys Arg Glu Asp Ala Gly Thr Tyr Trp Cys Glu Val Phe Asn Pro Ile
65                  70                  75                  80

Ser Lys Asn Gln Ser Asp Pro Ile Met Leu Asn
                85                  90

<210> SEQ ID NO 10
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM6 domain #1 (Ig-like V-type N-domain)

<400> SEQUENCE: 10

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105

<210> SEQ ID NO 11
<211> LENGTH: 88
<212> TYPE: PRT
<213> ORGANISM: Homo Sapiens
<220> FEATURE:
<221> NAME/KEY: MISC_FEATURE
<223> OTHER INFORMATION: CEACAM6 domain #2 (Ig-like C2-type 1)

<400> SEQUENCE: 11

Pro Lys Pro Ser Ile Ser Ser Asn Asn Ser Asn Pro Val Glu Asp Lys
1               5                   10                  15

Asp Ala Val Ala Phe Thr Cys Glu Pro Glu Val Gln Asn Thr Thr Tyr
            20                  25                  30

Leu Trp Trp Val Asn Gly Gln Ser Leu Pro Val Ser Pro Arg Leu Gln
        35                  40                  45

```
Leu Ser Asn Gly Asn Met Thr Leu Thr Leu Leu Ser Val Lys Arg Asn
 50                  55                  60

Asp Ala Gly Ser Tyr Glu Cys Glu Ile Gln Asn Pro Ala Ser Ala Asn
 65                  70                  75                  80

Arg Ser Asp Pro Val Thr Leu Asn
                 85
```

<210> SEQ ID NO 12
<211> LENGTH: 78
<212> TYPE: PRT
<213> ORGANISM: Homo Sapiens
<220> FEATURE:
<221> NAME/KEY: MISC_FEATURE
<223> OTHER INFORMATION: CEACAM6 domain #3 (Ig-like C2-type 2)

<400> SEQUENCE: 12

```
Pro Asp Val Pro Thr Ile Ser Pro Ser Lys Ala Asn Tyr Arg Pro Gly
 1               5                  10                  15

Glu Asn Leu Asn Leu Ser Cys His Ala Ala Ser Asn Pro Pro Ala Gln
                 20                  25                  30

Tyr Ser Trp Phe Ile Asn Gly Thr Phe Gln Gln Ser Thr Gln Glu Leu
             35                  40                  45

Phe Ile Pro Asn Ile Thr Val Asn Asn Ser Gly Ser Tyr Met Cys Gln
 50                  55                  60

Ala His Asn Ser Ala Thr Gly Leu Asn Arg Thr Thr Val Thr
 65                  70                  75
```

<210> SEQ ID NO 13
<211> LENGTH: 110
<212> TYPE: PRT
<213> ORGANISM: Homo Sapiens
<220> FEATURE:
<221> NAME/KEY: MISC_FEATURE
<223> OTHER INFORMATION: CEACAM5 domain #1 (Ig-like V-type N-domain)

<400> SEQUENCE: 13

```
Lys Leu Thr Ile Glu Ser Thr Pro Phe Asn Val Ala Glu Gly Lys Glu
 1               5                  10                  15

Val Leu Leu Leu Val His Asn Leu Pro Gln His Leu Phe Gly Tyr Ser
                 20                  25                  30

Trp Tyr Lys Gly Glu Arg Val Asp Gly Asn Arg Gln Ile Ile Gly Tyr
             35                  40                  45

Val Ile Gly Thr Gln Gln Ala Thr Pro Gly Pro Ala Tyr Ser Gly Arg
 50                  55                  60

Glu Ile Ile Tyr Pro Asn Ala Ser Leu Leu Ile Gln Asn Ile Ile Gln
 65                  70                  75                  80

Asn Asp Thr Gly Phe Tyr Thr Leu His Val Ile Lys Ser Asp Leu Val
                 85                  90                  95

Asn Glu Glu Ala Thr Gly Gln Phe Arg Val Tyr Pro Glu Leu
                100                 105                 110
```

<210> SEQ ID NO 14
<211> LENGTH: 92
<212> TYPE: PRT
<213> ORGANISM: Homo Sapiens
<220> FEATURE:
<221> NAME/KEY: MISC_FEATURE
<223> OTHER INFORMATION: CEACAM5 domain #2 (Ig-like C2-type 1)

```
<400> SEQUENCE: 14

Lys Pro Ser Ile Ser Ser Asn Asn Ser Lys Pro Val Glu Asp Lys Asp
1               5                   10                  15

Ala Val Ala Phe Thr Cys Glu Pro Glu Thr Gln Asp Ala Thr Tyr Leu
            20                  25                  30

Trp Trp Val Asn Asn Gln Ser Leu Pro Val Ser Pro Arg Leu Gln Leu
        35                  40                  45

Ser Asn Gly Asn Arg Thr Leu Thr Leu Phe Asn Val Thr Arg Asn Asp
    50                  55                  60

Thr Ala Ser Tyr Lys Cys Glu Thr Gln Asn Pro Val Ser Ala Arg Arg
65                  70                  75                  80

Ser Asp Ser Val Ile Leu Asn Val Leu Tyr Gly Pro
                85                  90

<210> SEQ ID NO 15
<211> LENGTH: 85
<212> TYPE: PRT
<213> ORGANISM: Homo Sapiens
<220> FEATURE:
<221> NAME/KEY: MISC_FEATURE
<223> OTHER INFORMATION: CEACAM5 domain #3 (Ig-like C2-type 2)

<400> SEQUENCE: 15

Asp Ala Pro Thr Ile Ser Pro Leu Asn Thr Ser Tyr Arg Ser Gly Glu
1               5                   10                  15

Asn Leu Asn Leu Ser Cys His Ala Ala Ser Asn Pro Pro Ala Gln Tyr
            20                  25                  30

Ser Trp Phe Val Asn Gly Thr Phe Gln Gln Ser Thr Gln Glu Leu Phe
        35                  40                  45

Ile Pro Asn Ile Thr Val Asn Asn Ser Gly Ser Tyr Thr Cys Gln Ala
    50                  55                  60

His Asn Ser Asp Thr Gly Leu Asn Arg Thr Thr Val Thr Thr Ile Thr
65                  70                  75                  80

Val Tyr Ala Glu Pro
                85

<210> SEQ ID NO 16
<211> LENGTH: 92
<212> TYPE: PRT
<213> ORGANISM: Homo Sapiens
<220> FEATURE:
<221> NAME/KEY: MISC_FEATURE
<223> OTHER INFORMATION: CEACAM5 domain #4 (Ig-like C2-type 3)

<400> SEQUENCE: 16

Lys Pro Phe Ile Thr Ser Asn Asn Ser Asn Pro Val Glu Asp Glu Asp
1               5                   10                  15

Ala Val Ala Leu Thr Cys Glu Pro Glu Ile Gln Asn Thr Thr Tyr Leu
            20                  25                  30

Trp Trp Val Asn Asn Gln Ser Leu Pro Val Ser Pro Arg Leu Gln Leu
        35                  40                  45

Ser Asn Asp Asn Arg Thr Leu Thr Leu Leu Ser Val Thr Arg Asn Asp
    50                  55                  60

Val Gly Pro Tyr Glu Cys Gly Ile Gln Asn Glu Leu Ser Val Asp His
65                  70                  75                  80

Ser Asp Pro Val Ile Leu Asn Val Leu Tyr Gly Pro
                85                  90
```

```
<210> SEQ ID NO 17
<211> LENGTH: 83
<212> TYPE: PRT
<213> ORGANISM: Homo Sapiens
<220> FEATURE:
<221> NAME/KEY: MISC_FEATURE
<223> OTHER INFORMATION: CEACAM5 domain #5 (Ig-like C2-type 4)

<400> SEQUENCE: 17

Asp Asp Pro Thr Ile Ser Pro Ser Tyr Thr Tyr Tyr Arg Pro Gly Val
1               5                   10                  15

Asn Leu Ser Leu Ser Cys His Ala Ala Ser Asn Pro Pro Ala Gln Tyr
            20                  25                  30

Ser Trp Leu Ile Asp Gly Asn Ile Gln Gln His Thr Gln Glu Leu Phe
        35                  40                  45

Ile Ser Asn Ile Thr Glu Lys Asn Ser Gly Leu Tyr Thr Cys Gln Ala
    50                  55                  60

Asn Asn Ser Ala Ser Gly His Ser Arg Thr Thr Val Lys Thr Ile Thr
65                  70                  75                  80

Val Ser Ala

<210> SEQ ID NO 18
<211> LENGTH: 92
<212> TYPE: PRT
<213> ORGANISM: Homo Sapiens
<220> FEATURE:
<221> NAME/KEY: MISC_FEATURE
<223> OTHER INFORMATION: CEACAM5 domain #6 (Ig-like C2-type 5)

<400> SEQUENCE: 18

Lys Pro Ser Ile Ser Ser Asn Asn Ser Lys Pro Val Glu Asp Lys Asp
1               5                   10                  15

Ala Val Ala Phe Thr Cys Glu Pro Glu Ala Gln Asn Thr Thr Tyr Leu
            20                  25                  30

Trp Trp Val Asn Gly Gln Ser Leu Pro Val Ser Pro Arg Leu Gln Leu
        35                  40                  45

Ser Asn Gly Asn Arg Thr Leu Thr Leu Phe Asn Val Thr Arg Asn Asp
    50                  55                  60

Ala Arg Ala Tyr Val Cys Gly Ile Gln Asn Ser Val Ser Ala Asn Arg
65                  70                  75                  80

Ser Asp Pro Val Thr Leu Asp Val Leu Tyr Gly Pro
                85                  90

<210> SEQ ID NO 19
<211> LENGTH: 84
<212> TYPE: PRT
<213> ORGANISM: Homo Sapiens
<220> FEATURE:
<221> NAME/KEY: MISC_FEATURE
<223> OTHER INFORMATION: CEACAM5 domain #7 (Ig-like C2-type 6)

<400> SEQUENCE: 19

Asp Thr Pro Ile Ile Ser Pro Pro Asp Ser Ser Tyr Leu Ser Gly Ala
1               5                   10                  15

Asn Leu Asn Leu Ser Cys His Ser Ala Ser Asn Pro Ser Pro Gln Tyr
            20                  25                  30

Ser Trp Arg Ile Asn Gly Ile Pro Gln Gln His Thr Gln Val Leu Phe
        35                  40                  45

Ile Ala Lys Ile Thr Pro Asn Asn Asn Gly Thr Tyr Ala Cys Phe Val
    50                  55                  60
```

-continued

Ser Asn Leu Ala Thr Gly Arg Asn Asn Ser Ile Val Lys Ser Ile Thr
 65                  70                  75                  80

Val Ser Ala Ser

<210> SEQ ID NO 20
<211> LENGTH: 873
<212> TYPE: PRT
<213> ORGANISM: Morayella catarrhalis
<220> FEATURE:
<221> NAME/KEY: MISC_FEATURE
<223> OTHER INFORMATION: NCBI accession number AAF40122

<400> SEQUENCE: 20

Met Asn Lys Ile Tyr Lys Val Lys Lys Asn Ala Ala Gly His Leu Val
  1               5                  10                  15

Ala Cys Ser Glu Phe Ala Lys Gly His Thr Lys Lys Ala Val Leu Gly
             20                  25                  30

Ser Leu Leu Ile Val Gly Ile Leu Gly Met Ala Thr Thr Ala Ser Ala
         35                  40                  45

Gln Gln Thr Ile Ala Arg Gln Gly Lys Gly Met His Ser Ile Ile Gly
     50                  55                  60

Gly Gly Asn Asp Asn Glu Ala Asn Gly Asp Tyr Ser Thr Val Ser Gly
 65                  70                  75                  80

Gly Asp Tyr Asn Glu Ala Lys Gly Asp Ser Ser Thr Ile Gly Gly Gly
                 85                  90                  95

Tyr Tyr Asn Glu Ala Asn Gly Asp Ser Ser Thr Ile Gly Gly Gly Phe
            100                 105                 110

Tyr Asn Glu Ala Lys Gly Glu Ser Ser Thr Ile Gly Gly Gly Asp Asn
        115                 120                 125

Asn Ser Ala Thr Gly Met Tyr Ser Thr Ile Gly Gly Gly Asp Asn Asn
130                 135                 140

Ser Ala Thr Gly Arg Tyr Ser Thr Ile Ala Gly Gly Trp Leu Asn Gln
145                 150                 155                 160

Ala Thr Gly His Ser Ser Thr Val Ala Gly Gly Trp Leu Asn Gln Ala
                165                 170                 175

Thr Asn Glu Asn Ser Thr Val Gly Gly Gly Arg Phe Asn Gln Ala Thr
            180                 185                 190

Gly Arg Asn Ser Thr Val Ala Gly Gly Tyr Lys Asn Lys Ala Thr Gly
        195                 200                 205

Val Asp Ser Thr Ile Ala Gly Gly Arg Asn Asn Gln Ala Asn Gly Ile
210                 215                 220

Gly Ser Phe Ala Ala Gly Ile Asp Asn Gln Ala Asn Ala Asn Asn Thr
225                 230                 235                 240

Val Ala Leu Gly Asn Lys Asn Ile Ile Lys Gly Lys Asp Ser Val Ala
                245                 250                 255

Ile Gly Ser Asn Asn Thr Val Glu Thr Gly Lys Glu Asn Val Phe Ile
            260                 265                 270

Leu Gly Ser Asn Thr Lys Asp Ala His Ser Asn Ser Val Leu Leu Gly
        275                 280                 285

Asn Glu Thr Thr Gly Lys Ala Ala Thr Thr Val Glu Asn Ala Lys Val
    290                 295                 300

Gly Gly Leu Ser Leu Thr Gly Phe Val Gly Ala Ser Lys Ala Asn Thr
305                 310                 315                 320

Asn Asn Gly Thr Val Ser Val Gly Lys Gln Gly Lys Glu Arg Gln Ile
                325                 330                 335

-continued

Val Asn Val Gly Ala Gly Gln Ile Arg Ala Asp Ser Thr Asp Ala Val
            340                 345                 350

Asn Gly Ser Gln Leu His Ala Leu Ala Thr Ala Val Asp Ala Glu Phe
        355                 360                 365

Arg Thr Leu Thr Gln Thr Gln Asn Ala Leu Ile Glu Gln Gly Glu Ala
    370                 375                 380

Ile Asn Gln Glu Leu Glu Gly Leu Ala Asp Tyr Thr Asn Ala Gln Asp
385                 390                 395                 400

Glu Lys Ile Leu Lys Asn Gln Thr Asp Ile Thr Ala Asn Lys Thr Ala
                405                 410                 415

Ile Glu Gln Asn Phe Asn Arg Thr Val Thr Asn Gly Phe Glu Ile Glu
            420                 425                 430

Lys Asn Lys Ala Gly Ile Ala Lys Asn Gln Ala Asp Ile Gln Thr Leu
        435                 440                 445

Glu Asn Asp Val Gly Lys Glu Leu Leu Asn Leu Ser Gly Arg Leu Leu
    450                 455                 460

Asp Gln Lys Ala Asp Ile Asp Asn Asn Ile Asn Asn Ile Tyr Glu Leu
465                 470                 475                 480

Ala Gln Gln Gln Asp Gln His Ser Ser Asp Ile Lys Thr Leu Lys Asn
                485                 490                 495

Asn Val Glu Glu Gly Leu Leu Asp Leu Ser Gly Arg Leu Ile Asp Gln
            500                 505                 510

Lys Ala Asp Leu Thr Lys Asp Ile Lys Ala Leu Glu Asn Asn Val Glu
        515                 520                 525

Glu Gly Leu Leu Asp Leu Ser Gly Arg Leu Ile Asp Gln Lys Ala Asp
    530                 535                 540

Ile Ala Lys Asn Gln Ala Asp Ile Gln Asp Leu Ala Ala Tyr Asn Glu
545                 550                 555                 560

Leu Gln Asp Gln Tyr Ala Gln Lys Gln Thr Glu Ala Ile Asp Ala Leu
                565                 570                 575

Asn Lys Ala Ser Ser Ala Asn Thr Asp Arg Ile Ala Thr Ala Glu Leu
            580                 585                 590

Gly Ile Ala Glu Asn Lys Lys Asp Ala Gln Ile Ala Lys Ala Gln Ala
        595                 600                 605

Asn Glu Asn Lys Asp Gly Ile Ala Lys Asn Gln Ala Asp Ile Ala Asn
    610                 615                 620

Asn Ile Lys Asn Ile Tyr Glu Leu Ala Gln Gln Gln Asp Gln His Ser
625                 630                 635                 640

Ser Asp Ile Lys Thr Leu Ala Lys Val Ser Ala Ala Asn Thr Asp Arg
                645                 650                 655

Ile Ala Lys Asn Lys Ala Glu Ala Asp Ala Ser Phe Glu Thr Leu Thr
            660                 665                 670

Lys Asn Gln Asn Thr Leu Ile Glu Gln Gly Glu Ala Leu Val Glu Gln
        675                 680                 685

Asn Lys Ala Ile Asn Gln Glu Leu Glu Gly Phe Ala Ala His Ala Asp
    690                 695                 700

Val Gln Asp Lys Gln Ile Leu Gln Asn Gln Ala Asp Ile Thr Ala Asn
705                 710                 715                 720

Lys Thr Ala Ile Glu Gln Asn Ile Asn Arg Thr Val Ala Asn Gly Phe
                725                 730                 735

Glu Ile Glu Lys Asn Lys Ala Gly Ile Ala Thr Asn Lys Gln Glu Leu
            740                 745                 750

```
Ile Leu Gln His Asp Arg Leu Asn Arg Ile Asn Glu Thr Asn Asn Arg
            755                 760                 765
Gln Asp Gln Lys Ile Asp Gln Leu Gly Tyr Ala Leu Lys Glu Gln Gly
    770                 775                 780
Gln His Phe Asn Asn Arg Ile Ser Ala Val Glu Arg Gln Thr Ala Gly
785                 790                 795                 800
Gly Ile Ala Asn Ala Ile Ala Ile Ala Thr Leu Pro Ser Pro Ser Arg
                805                 810                 815
Ala Gly Glu His His Val Leu Phe Gly Ser Gly Tyr His Asn Gly Gln
            820                 825                 830
Ala Ala Val Ser Leu Gly Ala Ala Gly Leu Ser Asp Thr Gly Lys Ser
            835                 840                 845
Thr Tyr Lys Ile Gly Leu Ser Trp Ser Asp Ala Gly Gly Leu Ser Gly
    850                 855                 860
Gly Val Gly Gly Ser Tyr Arg Trp Lys
865                 870

<210> SEQ ID NO 21
<211> LENGTH: 5
<212> TYPE: PRT
<213> ORGANISM: Homo Sapiens

<400> SEQUENCE: 21

Asn Arg Gln Ile Val
1               5

<210> SEQ ID NO 22
<211> LENGTH: 5
<212> TYPE: PRT
<213> ORGANISM: Homo Sapiens

<400> SEQUENCE: 22

Asn Arg Gln Ile Ile
1               5

<210> SEQ ID NO 23
<211> LENGTH: 5
<212> TYPE: PRT
<213> ORGANISM: Homo Sapiens

<400> SEQUENCE: 23

Gln Asn Asp Thr Gly
1               5

<210> SEQ ID NO 24
<211> LENGTH: 6
<212> TYPE: PRT
<213> ORGANISM: Homo Sapiens

<400> SEQUENCE: 24

Gly Tyr Ser Trp Tyr Lys
1               5
```